United States Patent [19]

Allgeier

[11] Patent Number: 5,134,134
[45] Date of Patent: Jul. 28, 1992

[54] UNSATURATED AMINODICARBOXYLIC ACID DERIVATIVES

[75] Inventor: Hans Allgeier, Lörrach-Haagen, Fed. Rep. of Germany

[73] Assignee: Ciba-Geigy Corporation, Ardsley, N.Y.

[21] Appl. No.: 699,412

[22] Filed: May 13, 1991

Related U.S. Application Data

[63] Continuation-in-part of Ser. No. 503,338, Apr. 2, 1990, abandoned.

[30] Foreign Application Priority Data

Apr. 7, 1989 [CH] Switzerland .................. 1317/89

[51] Int. Cl.$^5$ .................................. A61K 31/66
[52] U.S. Cl. ............................. 514/114; 560/171; 560/145; 514/113; 558/418; 558/420; 562/11
[58] Field of Search ............... 514/113, 114; 560/171, 560/145; 562/11; 558/418, 420

[56] References Cited

U.S. PATENT DOCUMENTS

| | | | |
|---|---|---|---|
| 4,399,287 | 8/1983 | Baillie et al. | 514/119 |
| 4,469,643 | 9/1984 | Tsuruoka et al. | 562/11 |
| 4,477,391 | 10/1984 | Collins | 562/11 |
| 4,483,853 | 11/1984 | Collins et al. | 514/113 |
| 4,761,405 | 8/1988 | Rzeszotarski et al. | 514/114 |
| 4,776,875 | 10/1988 | Löher et al. | 514/113 |
| 4,916,125 | 4/1990 | Herrling et al. | 514/114 |

FOREIGN PATENT DOCUMENTS

| | | | |
|---|---|---|---|
| 233154 | 8/1987 | European Pat. Off. | 514/113 |
| 302826 | 2/1989 | European Pat. Off. | 514/113 |
| 391850 | 10/1990 | European Pat. Off. | 514/113 |
| 3609818 | 9/1987 | Fed. Rep. of Germany | 514/113 |
| 53-087314 | 1/1977 | Japan | 514/113 |
| 8706131 | 2/1987 | PCT Int'l Appl. | 514/113 |

OTHER PUBLICATIONS

Br. J. Pharmacol. 99, 791-797 (1990).
Agrar. Biol. Chem. 40, 1905-1906 (1976).
Agrar. Biol. Chem. 41, 573-579 (1977).
Pol. J. Pharmacol. Pharm. 37, 575-584 (1985).

*Primary Examiner*—James H. Reamer
*Attorney, Agent, or Firm*—Irving M. Fishman; Karen G. Kaiser

[57] ABSTRACT

Unsaturated aminodicarboxylic acid derivatives of formula I

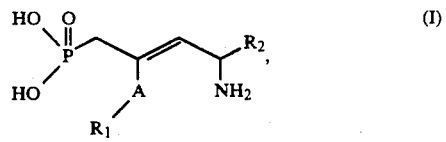

wherein A is a divalent aliphatic hydrocarbon radical containing 2 carbon atoms and $R_1$ and $R_2$ are each independently of the other free or esterified carboxyl groups, and salts thereof, have a pronounced and selective antagonistic action against N-methyl-D-aspartic acid (NMDA)-sensitive excitatory amino acid receptors. These compounds are prepared, for example, by converting, in a formula of formula II

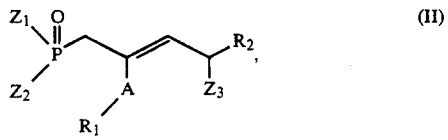

wherein $Z_1$ and $Z_2$ are hydroxy or protected hydroxy and $Z_3$ is protected amino, $Z_3$ into amino and, if present, converting protected hydroxyl groups $Z_1$ and/or $Z_2$ into hydroxy and, if desired, converting a resultant compound into another compound of formula I, resolving a resultant mixture of isomers into the individual components and separating the desired preferred isomer and/or converting a resultant free compound into a salt or a resultant salt into the corresponding free compound.

10 Claims, No Drawings

UNSATURATED AMINODICARBOXYLIC ACID DERIVATIVES

This is a Continuation-In-Part of our co-pending patent application Ser. No. 503,338, filed Apr. 2, 1990 now abandoned.

The present invention relates to unsaturated aminodicarboxylic derivatives of formula I

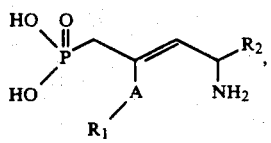

wherein A is a divalent aliphatic hydrocarbon radical containing 2 carbon atoms and $R_1$ and $R_2$ are each independently of the other free or esterified carboxyl groups, and to salts thereof, to the preparation of said compounds, to pharmaceutical compositions containing them, and to the use thereof as medicinal agents.

Divalent aliphatic hydrocarbon radicals containing 2 carbon atoms are, typically, 1,2-ethylene or 1,2-vinylene.

Esterfied carboxy is, typically, carboxy esterified with an aliphatic or araliphatic alcohol and is lower alkoxycarbonyl or phenyl-lower alkoxycarbonyl which is unsubstituted or substituted, for example, by lower alkyl, lower alkoxy, halogen, cyano and/or trifluoromethyl, and the phenyl moiety of phenyl-lower alkoxycarbonyl $R_2$ may carry one or more, for example two or three, of the cited substituents.

Throughout this specification, radicals and compounds qualified by the term "lower" will be understood as meaning, for example, those containing up to and including 4 carbon atoms. Lower alkyl may be $C_1$-$C_7$alkyl, preferably $C_1$-$C_4$alkyl such as preferably methyl or, less preferably, ethyl, propyl, isopropyl or butyl, but may also be isobutyl, sec.-butyl, tert.-butyl or $C_1$-$C_5$alkyl such as pentyl, hexyl or heptyl.

Lower alkoxy may be $C_1$-$C_7$alkoxy, preferably $C_1$-$C_4$alkoxy such as methoxy, ethoxy, propyloxy, isopropyloxy or butyloxy, but may also be isobutyloxy, sec.-butyloxy, tert.-butyloxy or pentyloxy, hexyloxy or heptyloxy.

Lower alkoxycarbonyl may be $C_1$-$C_7$alkoxycarbonyl, preferably $C_1$-$C_4$alkoxycarbonyl such as methoxycarbonyl, ethoxycarbonyl, propoxycarbonyl, isopropoxycarbonyl or butoxycarbonyl, but may also be a $C_5$-$C_7$-alkoxyisopropoxycarbonyl or butoxycarbonyl group, and also a $C_5$-$C_7$-alkoxycarbonyl group such as pentyloxycarbonyl, hexyloxycarbonyl or heptyloxycarbonyl group.

Phenyl-lower alkoxycarbonyl may be phenyl-$C_1$-$C_4$alkoxycarbonyl such as benzyloxycarbonyl, 2-phenylethoxycarbonyl or, less preferably, 3-phenylpropoxycarbonyl or 4-phenylbutoxycarbonyl.

Halogen is typically, halogen having an atomic number of up to 35 inclusive, such as chloro or fluoro and also bromo.

On account of their amphoteric character, the compounds of formula I are obtained in the form of their inner salts and can form acid addition salts as well as salts with bases.

Representative examples of acid addition salts of compounds of formula I are the pharmaceutically acceptable salts thereof with suitable mineral acids such as hydrohalic acids, sulfuric acid or phosphoric acid, for example hydrochlorides, hydrobromides, sulfates, hydrogen sulfates or phosphates, or salts with suitable aliphatic or aromatic sulfonic acids or N-substituted sulfamic acids, for example methanesulfonates, benzenesulfonates, p-tosylates or N-cyclohexylsulfaminates (cyclamates).es( Salts of compounds of formula I are in particular the salts thereof with pharmaceutically acceptable bases, such as non-toxic metal salts derived from metals of groups Ia, Ib, IIa and IIb, e.g. alkali metal salts, preferably sodium or potassium salts, alkaline earth metal salts, preferably calcium or magnesium salts, copper, aluminium or zinc salts, and also ammonium salts with ammonia or organic amines or quaternary ammonium bases such as free or C-hydroxylated aliphatic amines, preferably mono-, di-or tri-lower alkylamines, e.g. methylamine, ethylamine, dimethylamine or diethylamine, mono-, di- or tri(hydroxylower alkyl)amines such as ethanolamine, diethanolamine or triethanolamine, tris-(hydroxymethyl)aminomethane or 2-hydroxy-tert.-butylamine, or N-(hydroxy-lower alkyl)-N,N-di-lower alkylamines or N-(polyhydroxy-lower alkyl)-N-lower alkylamines such as 2-(dimethylamino)ethanol or D-glucamine, or quaternary aliphatic ammonium hydroxides, e.g. with tetrabutylammonium hydroxide.

For isolation or purification it is also possible to use pharmaceutically unsuitable salts. For therapeutic use, only the pharmaceutically acceptable non-toxic salts are suitable, for which reason they are preferred.

The compounds of formula I have valuable pharmacological properties. In particular they have a marked and selective antagonistic action against N-methyl-D-aspartic acid sensitive (NMDA-sensitive) excitatory amino acid receptors of warm-blooded animals. This can be determined in vitro, for example in the experimental procedure of G. Fagg and A. Matus, Proc. Nat. Acad. Sci., USA, 81, 6876–80 (1984). In this procedure, it is determined to what extent the binding of L-$^3$H-glutamic acid to NMDA receptors is inhibited. The NMDA antagonistic properties can, however, also be demonstrated in vivo, for example in mice, by means of the inhibitory action on NMDA-induced convulsions.

The anticonvulsive properties of the compounds of this invention can be determined, for example, in mice by means of their marked protective action against convulsions induced by electroshock or audiogenically induced convulsions, for which purpose, for example, the established electroshock mouse model or the experimental procedure of Chapman et al., Arzneimittel-Forsch. 34, 1261 (1984) may be used. The compounds of this invention are distinguished in these procedures, especially in the electroshock mouse model, by improved activity as compared with structurally related compounds.

Owing to these properties, the compounds of formula I and the pharmaceutically acceptable salts thereof are most suitable for the treatment of pathological states which respond to a blocking of NMDA-sensitive receptors, for example of cerebral ischaemia, ischaemic diseases of the eye, muscle spasms such as local or general spasticity and, in particular, of convulsions. The invention relates in particular to compounds of formula I, wherein A is lower alkylene or lower alkenylene containing 2 carbon atoms, and $R_1$ and $R_2$ are each independently of the other carboxy, lower alkoxycarbonyl or phenyl-lower alkoxycarbonyl which is unsubstituted or substituted by lower alkyl, lower alkoxy, halogen, cyano and/or trifluoromethyl and the salts thereof.

More particularly, the invention relates to compounds of formula I, wherein A is 1,2-ethylene or 1,2-vinylene, $R_1$ is carboxy, $C_1$-$C_4$alkoxycarbonyl such as methoxycarbonyl or ethoxycarbonyl, or phenyl-$C_1$-$C_4$alkoxycarbonyl which is unsubstituted or substituted by $C_1$-$C_4$alkyl such as methyl, $C_1$-$C_4$alkoxy such as methoxy, halogen having an atomic number of up to 35 inclusive, such as fluoro or chloro, cyano and/or trifluoromethyl, for example benzyl- or 2-phenylethoxycarbonyl, and $R_2$ is carboxy, $C_1$-$C_4$alkoxycarbonyl such as methoxycarbonyl or ethoxycarbonyl, or phenyl-$C_1$-$C_4$-alkoxycarbonyl which is unsubstituted or substituted by $C_1$-$C_4$alkyl such as methyl, $C_1$-$C_4$alkoxy such methoxy, halogen having an atomic number of up to 35 inclusive, such as fluoro or chloro, cyano and/or trifluoromethyl, for example benzyl- or 2-phenylethoxycarbonyl, and their salts, preferably their pharmaceutically acceptable salts.

First and foremost, the invention relates to compounds of formula I, wherein A is 1,2-ethylene, and $R_1$ and $R_2$ are identical or different $C_1$-$C_4$alkoxycarbonyl or phenyl-$C_1$-$C_4$-alkoxycarbonyl groups such as methoxycarbonyl, ethoxycarbonyl or benzyloxycarbonyl, and their salts, especially their pharmaceutically acceptable, salts.

Specifically, the invention relates to the compounds of formula I and their salts, preferably pharmaceutically acceptable salts, named in the Examples.

The process for the preparation of the compounds of this invention comprises converting, in a compound of formula II

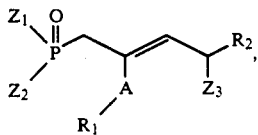

(II)

wherein $Z_1$ and $Z_2$ are hydroxy or protected hydroxy and $Z_3$ is protected amino, $Z_3$ into amino and, if present, converting protected hydroxyl groups $Z_1$ and/or $Z_2$ into hydroxy and, if desired, converting a resultant compound into another compound of formula I, resolving a resultant mixture of isomers into the individual components and separating the desired preferred isomer and/or converting a resultant free compound into a salt or a resultant salt into the corresponding free compound.

In starting compounds of formula II, protected hydroxy $Z_1$ and/or $Z_2$ may be etherified hydroxy, preferably aliphatic etherified hydroxy, for example lower alkoxy such as methoxy, ethoxy or, preferably, isopropyloxy, and protected amino $Z_3$ may be acylated or silylated amino.

The acyl group in acylated amino may be derived from an organic acid such as an aliphatic or aromatic mono- or dicarboxylic acid or from an aliphatic, araliphatic or aromatic half-ester of carbonic acid. Acylated amino may therefore be lower alkanoylamino such as formylamino, acetylamino or pivaloylamino, benzoylamino which is unsubstituted or substituted by lower alkyl, lower alkoxy, halogen and/or nitro, lower alkoxycarbamoyl such as methoxy-, ethoxy or tert.-butoxycarbamoyl, phenyl-lower alkoxycarbamoyl which may be substituted in the phenyl moiety by lower alkyl, lower alkoxy, halogen and/or nitro, for example benzyloxycarbamoyl, or phenoxycarbamoyl which is substituted by lower alkyl, lower alkoxy, halogen and/or nitro.

Silylated amino may be tri-lower alkylsilylamino such as trimethylsilylamino or tributylsilylamino.

The liberation of the protected groups from compounds of formula II, i.e. of hydroxy from protected hydroxyl groups $Z_1$ and/or $Z_2$ and/or of amino from protected amino groups $Z_3$, may be effected by treatment with an acid agent, for example a tri-lower alkylhalosilane such as trimethylbromosilane, tributylbromosilane or trimethyliodosilane or, in particular for the preparation of compounds of formula I, wherein $R_1$ and $R_2$ are carboxy, with an aqueous mineral acid such as strong, for example 6-normal, hydrochloric acid. In the treatment with a tri-lower alkylhalosilane, it is preferred to use an inert solvent such as a halogenated aliphatic hydrocarbon, for example dichloromethane or, less preferably, tri- or tetrachloromethane, trichloroethane or tetrachloroethane, for example in the temperature range from approximately $-25°$ to approximately $+50°$ C., preferably from approximately $0°$ to $30°$ C., for example at room temperature, i.e. in the range from approximately $15°$ to $25°$ C., conveniently under essentially anhydrous conditions and in an inert gas atmosphere such as argon or nitrogen. Working up is conveniently effected by adding a hydrohalic acid acceptor, preferably an aliphatic epoxy compound such as an epoxy-lower alkane, for example propylene oxide in a lower alkanol such as ethanol. The treatment with an aqueous mineral acid is carried out preferably with heating, for example to a temperature in the range from approximately $60°$ to $120°$ C., preferably to boiling temperature.

A preferred embodiment of the process of the invention comprises starting from compounds of formula II, wherein $Z_1$ and $Z_2$ are lower alkoxy such as isopropyloxy, and $Z_3$ is lower alkanoylamino such as formylamino, or lower alkoxycarbamoyl such as tert.-butoxycarbamoyl, and treating said compounds in an aliphatic hydrocarbon such as dichloromethane, in the temperature range from approximately $15°$ to approximately $25°$ C., with a tri-lower alkylbromosilane such as trimethylbromosilane or tributylbromosilane, allowing the reaction mixture to react for some time, for example approximately 2 to 30 hours, then adding an ethanolic solution of propylene oxide, and isolating the product by filtration.

Starting materials of formula II may be prepared by reacting an $\alpha,\beta$-unsaturated aldehyde of formula IIa

(IIa)

with an $\alpha$-isocyanoacetate of formula IIb

(IIb)

in a manner known per se, for example in the presence of a copper or gold catalyst, for example of copper(I) oxide or, preferably, of bis(cyclohexylisocyanide) gold(I) tetrafluoroborate, in the presence of a compound of formula X

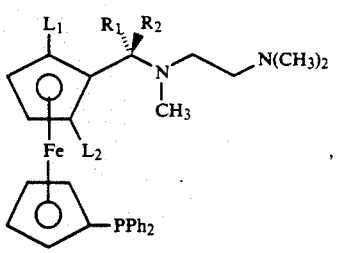

(X)

wherein one of the substituents $L_1$ and $L_2$ and $PPh_2$ is diphenylphosphino and the other is hydrogen, and one of the substituents $R_1$ and $R_2$ is methyl and the other is hydrogen, to the corresponding 5-substituted 2-oxazoline-4-carboxylate of formula IIc

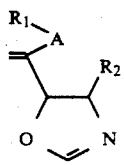

(IIc)

converting said compound of formula IIc by hydrolysis, for example in aqueous tetrahydrofuran, into the corresponding open-chain ester of formula IId

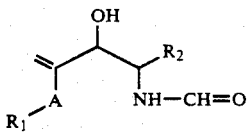

(IId)

converting said ester by treatment with thionyl bromide in a manner known per se into the corresponding ω-bromoester of formula IIe

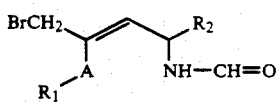

(IIe)

and further reacting said ester of formula (IIe), in a manner known per se, with a triphosphite of formula $P(Z_a)(Z_b)(Z_c)$, wherein $Z_a$, $Z_b$ and $Z_c$ are identical or different hydroxyl groups which are protected in an ether form, for example with a tri-lower alkylphosphite such as triisopropylphosphite, to the corresponding compound of formula II'

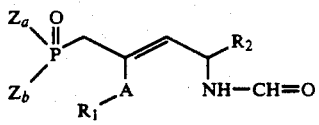

(II')

Compounds obtainable by the process of this invention can be converted in conventional manner into other compounds of formula I.

Thus in compounds of formula I, free and esterified carboxyl groups $R_1$ and $R_2$ can be converted in conventional manner into each other. In particular, it is possible to convert esterified carboxy by hydrolysis into carboxy or to convert free carboxy by reaction with an alcohol into esterified carboxy. Further, esterified carboxy can be transesterified to another esterified carboxy group.

The hydrolysis of carboxylic acid esters (I; $R_1$ and/or $R_2$=esterified carboxy) is carried out in conventional manner, if required in the presence of an acid, for example a mineral acid such as hydrochloric acid or sulfuric acid, or of a base such as an alkali metal hydroxide, for example sodium hydroxide.

The reaction of carboxylic acids (I; $R_1$ and/or $R_2$=carboxy) is carried out in conventional manner, if required in the presence of an acid, for example a mineral acid such as hydrochloric acid or sulfuric acid, if necessary in the presence of 4-(N,N-dimethylamino)-pyradine and/or of a condensing agent such as N,N-dicyclohexylcarbodiimide.

The transesterification of esters (I; $R_1$ and/or $R_2$=esterified carboxy) with alcohols is carried out in conventional manner under acid- or base-catalysed conditions, for example in the presence of a catalytic amount of a mineral acid such as hydrochloric acid or sulfuric acid, or by using the alcohol component in the form of a metal alcoholate, for example an alkali metal alcoholate.

Salts can be converted in a manner known per se into the free compounds, for example by treatment with a abase such as an alkali metal hydroxide, a metal carbonate or metal hydrogencarbonate, or ammonia, or with another salt-forming base initially mentioned or with an acid, for example a mineral acid such as hydrochloric acid, or with another salt-forming acid initially mentioned.

Salts can be converted in a manner known per se into other salts. For example, acid addition salts can be converted into other salts by treatment with a suitable metal salt, such as a sodium, barium or silver salt, of another acid in a suitable solvent in which an inorganic salt that forms is insoluble and therefore precipitates from the reaction mixture, and basic salts by liberating the free acid and renewed salt-formation.

The compounds of formula I, including their salts, can be also be obtained in the form of hydrates or may contain the solvent used for crystallization in their crystal structure.

Because of the close relationship between the novel compounds in the free form and in the form of their salts, the references made throughout this specification to the free compounds and their salts also apply by analogy to the corresponding salts and free compounds.

Resultant mixtures of diastereomers and mixtures of racemates can be separated in known manner into the pure diastereomers or racemates on the basis of the physico-chemical differences between the components, for example by chromatography and/or fractional crystallization. Resultant racemates can also be resolved into the optical antipodes by known methods, for example by recrystallization from an optically active solvent, with the aid of microorganisms or by reacting the mixture of diastereomers or racemate with an optically active compound, for example in accordance with the acid, basic or functionally modified groups present in compounds of formula I, with an optically active acid, base or an optically active alcohol, to form mixtures of diastereomers salts or functional derivatives such as esters, and separating the latter into the diastereomers from which the desired enantiomers can be isolated in the appropriate conventional manner.

Illustrative examples of bases, acids and alcohols suitable for this purpose are optically active alkaloid bases such as strychnine, cinchonine or brucine, or D-or L-(-1-phenyl)-ethylamine, 3-pipecoline, ephedrine, amphetamine and similar synthetically obtainable bases, optically active carboxylic or sulfonic acids such as quinic acid or D- or L-tartaric acid, di-o-toluyltartaric acid, malic acid, mandelic acid or camphorsulphonic acid, or optically active alcohols such as borneol or D- or L-(1-phenyl)ethanol.

The invention also relates to those embodiments of the process in which a compound obtainable as intermediate at any stage of the process is used as starting material and the remaining steps are carried out, or a starting material is used in the form of a salt or, preferably, is formed under the reaction conditions.

The invention also relates to novel starting materials developed specifically for the preparation of the compounds of the invention, especially the group of starting materials that result in the compounds of formula I referred to at the outset as being preferred, to processes for their preparation, and to their use as intermediates.

The novel compounds of formula I may be used for example in the form of pharmaceutical compositions that contain a therapeutically effective amount of active ingredient, optionally together with inorganic or organic, solid or liquid pharmaceutically acceptable carriers that are suitable for enteral, e.g. oral, or parenteral administration. Hence the compositions employed are tablets or gelatin capsules which contain the active ingredient together with diluents, e.g. lactose, dextrose, saccharose, mannitol, sorbitol, cellulose and/or lubricants, e.g. silica, talcum, stearic acid or salts thereof, such as magnesium or calcium stearate, and/or polyethylene glycol. Tablets may also contain binders, e.g. magnesium aluminium silicate, starches such as maize, corn, rice or arrow root starch, gelatin, tragacanth, methyl cellulose, sodium carboxymethylcellulose and/or polyvinylpyrrolidone and, if desired, disintegrators, e.g. starches, agar, alginic acid or a salt thereof such as sodium alginate, and/or effervescent mixtures, or adsorption agents, colorants, flavoring matters and sweeteners. The novel compounds of formula I may also be used in the form of compositions for parenteral administration or of infusion solutions. Such solutions are preferably isotonic aqueous solutions or suspensions which, e.g. in the case of lyophilized formulations that contain the active ingredient alone or together with a carrier, e.g. mannitol, may be prepared prior to use. The pharmaceutical compositions may be sterilized and/or may contain adjuvants, e.g. preservatives, stabilizers, wetting agents and/or emulsifiers, sublicenses, salts for regulating the osmotic pressure and/or buffers. The pharmaceutical compositions of the invention may, if desired, contain further pharmacologically active substances, are prepared in a manner known per se, e.g. by conventional mixing, granulating, confectioning, dissolving or lyophilizing methods, and contain from about 0.1 to 100%, preferably from about 1 to 50% (lyophilizates up to 100%), of active ingredient.

The invention also relates to the use of compounds of formula I, preferably in the form of pharmaceutical compositions. The dosage may depend on different factors, such as the mode of application, species, age and/or the individual condition of the patient. The daily doses for oral administration are in the range from about 0.25 to 10 mg/kg, and for warm-blooded animals having a body weight of about 70 kg, preferably in daily doses of about 20 mg to 500 mg.

The invention is illustrated by the following Examples. Pressures are given in mbar.

EXAMPLE 1

4.3 g (9.9 mmol) of diethyl E-2-formylamino-4-diisopropylphosphonomethyl-hept-3-ene-1,7-dicarboxylate are dissolved in 14 ml of dichloromethane and 5.2 ml (40 mmol) of trimethylbromosilane are added dropwise at room temperature to the solution. The reaction mixture is allowed to stand for 20 hours and, after addition of 14 ml of ethanol, allowed to stand for a further 19 hours. The reaction mixture is concentrated on a rotary evaporator and the residue is taken up in 14 ml of ethanol. After addition of 14 ml of propylene oxide and 14 ml of ethanol, the resultant suspension is stirred for 90 minutes and then filtered with suction, affording diethyl E-2-amino-4-phosphonomethyl-hept-3-ene-1,7 -dicarboxylate of m.p. 218°-220° C. (decomp.).

The starting material can be prepared as follows:

With stirring, 14.4 g (100 mmol) of ethyl 5-oxopentanoate, 9.2 g (112.6 mmol) of dimethylammonium chloride and 10.8 ml (117 mmol) of 37% formaldehyde solution are heated to 100° C. The mixture is cooled and extracted with 3×30 ml of diethyl ether. The batch is cooled and the organic phases are combined, washed with a saturated solution of sodium chloride, dried over magnesium sulfate and evaporated to dryness, giving ethyl 4-formylpent-4-enoate as a colorless oil which can be further reacted without additional purification.

14.9 g (95 mmol) of ethyl 4-formylpent-4-enoate and 10.4 g (95 mmol) of ethyl isocyanoacetate are added dropwise to a suspension of copper(I) oxide in 50 ml of benzene. After the the exothermic reaction has subsided, the mixture is stirred for 45 minutes at room temperature, filtered over Hyflo ® and evaporated to dryness. The residue is taken up in 75 ml of tetrahydrofuran, diluted with 25 ml of water, and the batch is heated to reflux for 4 hours with stirring. The batch is evaporated to dryness and the residue is chromatographed over slica gel with a 9:1 mixture of toluene/isopropanol as eluant, giving diethyl 2-formylamino-3-hydroxy-4-methylene-heptane-1,7-dicarboxylate as a brownish oil.

10.3 g (35.9 mmol) of diethyl 2-formylamino-3-hydroxy-4-methylene-heptane-1,7-dicarboxylate are dissolved in 100 ml of dichloromethane and 3.34 ml (43.1 mmol) of thionyl bromide are added dropwise to the solution at room temperature. After 1 hour, 10 ml of water are added and the batch is thoroughly stirred. The organic phase is separated, washed in succession with water, saturated potassium hydrogencarbonate solution and again with water, dried over magnesium sulfate and concentrated by evaporation, giving diethyl 2-formylamino-4-bromomethyl-hept-3-ene-1,7-dicarboxylate as a brownish oil.

8.7 g (25 mmol) of diethyl 2-formylamino-4-bromomethyl-hept-3-ene-1,7-dicarboxylate and 21 ml (75 mmol) of triisopropylphosphite (90%) are heated to 80°-90° C. and the mixture is stirred for 19 hours under a pressure of ca. 100 mbar. Excess triisopropylphosphite is removed by distillation and the residue obtained after evaporation is chromatographed over 150 g of silica gel first with ethyl acetate and then with ethyl acetate/ethanol (9:1) as eluant, giving diethyl E-2-formylamino-4-diisopropylphosphonomethyl-hept-3-ene-1,7-dicarboxylate as a yellowish oil.

EXAMPLE 2

1.3 g (4.0 mmol) of diethyl E-2-amino-4-phosphonomethyl-hept-3-ene-1,7-dicarboxylate are heated in 15 ml of water for 23 hours to reflux. The reaction mixture is concentrated to 7 ml and the residue is stirred in an ice bath. The precipitated product is isolated by filtration, affording E-2-amino-4-phosphonomethyl-hept-3-ene-1,7-dicarboxylic acid of m.p. 192° C. (dec.).

EXAMPLE 3

To 3.25 g (10 mmol) of diethyl E-2-amino-4-phosphonomethyl-hept-3-ene-1,7-dicarboxylate and 10.8 g (100 mmol) of benzyl alcohol are added 10 ml of methylene chloride and 20 ml of 4N ethereal hydrochloric acid, and the mixture is allowed to stand for 1 week. The mixture is then evaporated to dryness, and the residue is dissolved in 25 ml of ethanol. To this solution is then added dropwise a solution of 15 ml of propylene oxide in 15 ml of ethanol. The readily volatile constituents are removed by evaporation under reduced pressure, affording dibenzyl E-2-amino-4-phosphonomethyl-hept-3-ene-1,7-dicarboxylate.

EXAMPLE 4

To a suspension of 3.0 g (9.3 mmol) of diethyl E-2-amino-4-phosphonomethyl-hept-3-ene-1,7-dicarboxylate in 19.1 ml (185.6 mmol) of benzyl alcohol are added 40 ml of a 4N solution of hydrochloric acid in diethyl ether. The solution formed is allowed to stand for 1 week. The reaction mixture is evaporated to dryness. The residue is dissolved in 35 ml of ethanol, and a solution of 35 ml of propylene oxide in 35 ml of ethanol is added. The crystalline precipitate formed is collected, re-crystallized twice from water and dried over phosphorus pentoxide, affording dibenzyl E-2-amino-4-phosphonomethyl-hept-3-ene-1,7-dicarboxylate of m.p. 220°–221° (decomp).

EXAMPLE 5

Tablets which each contain 50 mg of diethyl E-2-amino-4-phosphonomethyl-hept-3-ene-1,7-dicarboxylate or a salt, for example the sodium salt, thereof, can be prepared as follows:

Composition (for 1000 tablets)

active ingredient: 500.0 g
lactose: 500.0 g
potato starch: 352.0 g
gelatin: 8.0 g
talcum: 60.0 g
magnesium stearate: 10.0 g
silica (highly dispersed): 20.0 g
ethanol: q.s.

The active ingredient is mixed with the lactose and 292 g of potato starch and this mixture is moistened with an ethanolic solution of the gelatin and granulated through a sieve. The granulate is dried and then mixed with the remainder of the potato starch, the talcum, the magnesium stearate and the highly disperse silica and the mixture is compressed to tablets weighing 145.0 g each and containing 50.0 mg of active ingredient. If desired, the tablets may be provided with a breaking notch for a finer adjustment of the dose.

EXAMPLE 6

Film-coated tablets which each contain 100 mg of diethyl E-2-amino-4-phosphonomethyl-hept-3-ene-1,7-dicarboxylate or a salt, for example the sodium salt, thereof, can be prepared as follows:

Composition (for 1000 tablets)

active ingredient: 100.00 g
lactose: 100.00 g
corn starch: 70.00 g
talcum: 8.50 g
calcium stearate: 1.50 g
hydroxypropylmethyl cellulose: 2.36 g
shellac: 0.64 g
water: q.s.
methylene chloride: q.s.

The active ingredient, the lactose and 40 g of the corn starch are mixed and moistened with a paste prepared from 15 g of corn starch and water (with heating) and the mixture is granulated. The granulate is dried and mixed with the remainder of the corn starch, talcum and the calcium stearate. The mixture is compressed to tablets weighing 280 g. The tablets are then coated with a solution of the hydroxypropylmethyl cellulose and the shellac in methylene chloride. The coated tablets have a final weight of 283 g.

EXAMPLE 7

Hard gelatin capsules containing 100 mg of active ingredient, for example diethyl E-2-amino-4-phosphonomethyl-hept-3-ene-1,7-dicarboxylate or a salt, for example the sodium salt, thereof, can be prepared as follows:

Composition (for 1000 capsules)

active ingredient: 100.0 g
lactose: 250.0 g
microcrystalline cellulose: 30.0 g
sodium lauryl sulfate: 2.0 g
magnesium stearate: 8.0 g The sodium lauryl sulfate is sieved through a sieve having a mesh size of 0.2 mm and added to the active ingredient (lyophilized) and both components are intimately mixed for 10 minutes. First the lactose is sieved through a sieve having a mesh size of 0.6 mm and then the microcrystalline cellulose is sieved through a sieve having a mesh size of 0.9 mm, added to the above mixture, and the ingredients are intimately mixed for 10 minutes. Finally, the magnesium is sieved through a sieve having a mesh size of 0.8 mm, added to the mixture, and all the ingredients are mixed for 3 minutes. Size 0 hard gelatin capsules are filled with 390 mg of this mixture.

EXAMPLE 8

A 0.2% injection or infusion solution of diethyl E-2-amino-4-phosphonomethyl-hept-3-ene-1,7-dicarboxylate or a salt, for example the sodium salt, thereof, can be prepared as follows:

Composition (for 1000 ampoules)

active ingredient: 5.0 g
sodium chloride: 22.5 g
phosphate buffer (pH=7.4): 300.0 g
demineralized water to make up: 2500.0 ml The active ingredient and the sodium chloride are dissolved in 1000 ml of water and filtered through a microfilter. The buffer solution is added, followed by the addition of water to make up 2500 ml. To prepare dosage unit forms, 1.0 or 2.5 ml of the solution are filled into glass ampoules (each containing 2.0 or 5.0 mg of active ingredient).

EXAMPLE 9

As described in the foregoing Examples 5 to 8, it is also possible to prepare pharmaceutical compositions containing another compound of formula I according to any one of the preceding Preparatory Examples.

What is claimed is:

1. An unsaturated aminodicarboxylic acid derivative of formula I,

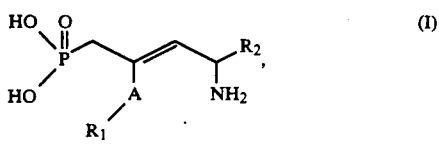

wherein A is a divalent aliphatic hydrocarbon radical containing 2 carbon atoms and $R_1$ and $R_2$ are each independently of the other free or esterified carboxyl groups, said esterified carboxyl groups selected from the group lower alkoxycarbonyl, phenyl-lower alkoxycarbonyl, and substituted phenyl-lower alkoxycarbonyl, said substituted phenyl-lower alkoxycarbonyl being substituted by lower alkyl, lower alkoxy, halogen, cyano, or trifluoromethyl, or a salt thereof.

2. A compound as claimed in claim 1 of formula I, wherein A is lower alkylene or lower alkenylene containing 2 carbon atoms, and $R_1$ and $R_2$ are each independently of the other carboxy, lower alkoxycarbonyl or phenyl-lower alkoxycarbonyl which is unsubstituted or substituted by lower alkyl, lower alkoxy, halogen, cyano and/or trifluoromethyl, or a salt thereof.

3. A compound as claimed in claim 1 of formula I, wherein A is 1,2-ethylene or 1,2-vinylene, $R_1$ is carboxy, $C_1$-$C_4$alkoxycarbonyl or phenyl-$C_1$-$C_4$alkoxycarbonyl which is unsubstituted or substituted by $C_1$-$C_4$alkyl, $C_1$-$C_4$alkoxy, halogen having an atomic number of up to 35 inclusive, and $R_2$ is carboxy, $C_1$-$C_4$alkoxycarbonyl or phenyl-$C_1$-$C_4$alkoxycarbonyl which is unsubstituted or substituted by $C_1$-$C_4$alkyl, $C_1$-$C_4$alkoxy, halogen having an atomic number of up to 35 inclusive, and/or trifluoromethyl, or a salt thereof.

4. A compound as claimed in claim 1 of formula I, wherein A is 1,2-ethylene, $R_1$ is carboxy, $C_1$-$C_4$alkoxycarbonyl or phenyl-$C_1$-$C_4$alkoxycarbonyl which is unsubstituted or substituted by $C_1$-$C_4$alkyl, $C_1$-$C_4$alkoxy, halogen having an atomic number of up to 35 inclusive, and $R_2$ is carboxy, $C_1$-$C_4$alkoxycarbonyl or phenyl-$C_1$-$C_4$alkoxycarbonyl which is unsubstituted or substituted by $C_1$-$C_4$alkyl, $C_1$-$C_4$alkoxy, halogen having an atomic number of up to 35 inclusive, and/or trifluoromethyl, or a salt thereof.

5. A compound as claimed in claim 1 of formula I, wherein A is 1,2-ethylene and $R_1$ and $R_2$ are identical or different $C_1$-$C_4$alkoxycarbonyl or phenyl-$C_1$-$C_4$alkoxycarbonyl groups, or a salt thereof.

6. A compound as claimed in claim 1 being diethyl E-2-amino-4-phosphonomethyl-hept-3-ene-1,7-dicarboxylate or a salt thereof.

7. A compound as claimed in claim 1 being E-2-amino-4-phosphonomethyl-hept-3-ene-1,7-dicarboxylic acid or a salt thereof.

8. A compound as claimed in claim 1 being dibenzyl E-2-amino-4-phosphonomethyl-hept-3-ene-1,7-dicarboxylate or a salt thereof.

9. A pharmaceutical composition containing a therapeutically effective amount of compound as claimed in claim 1 in the free form or in the form of a pharmaceutically acceptable salt, together with customary pharmaceutically acceptable excipients.

10. A method of treatment of of pathological states which respond to a blocking of NMDA-sensitive receptors, especially of convulsions, wherein an NMDA-sensitive receptor inhibiting effective amount of a compound as claimed in claim 1 is administered to a warm-blooded organism in need of such treatment.

* * * * *